United States Patent [19]
Kritz

[11] 4,296,482
[45] Oct. 20, 1981

[54] PARAMETRIC ARRAY DOPPLER SONAR APPARATUS

[75] Inventor: Jacob A. Kritz, Westbury, N.Y.

[73] Assignee: Sperry Corporation, New York, N.Y.

[21] Appl. No.: 133,158

[22] Filed: Mar. 24, 1980

[51] Int. Cl.³ .............................................. G01S 15/60
[52] U.S. Cl. ...................................... 367/91; 367/92; 367/150
[58] Field of Search .......................... 367/91, 92, 150

[56] References Cited
U.S. PATENT DOCUMENTS

| | | | |
|---|---|---|---|
| 3,510,833 | 5/1970 | Turner | 367/150 X |
| 3,886,487 | 5/1975 | Walsh et al. | 367/92 |

*Primary Examiner*—Richard A. Farley
*Attorney, Agent, or Firm*—Howard P. Terry; Joseph M. Roehl

[57] ABSTRACT

Parametric array Doppler sonar apparatus includes an acoustic lens containing a flat disk-like central portion and an annular outer portion serving as a convergent lens. Multiple transducers are positioned between the lens and the focal plane so as to launch collimated acoustic beams in specified directions through the central portion of the lens and to receive reflected energy propagating principally through the annular portion of the lens.

12 Claims, 6 Drawing Figures

PARAMETRIC ARRAY DOPPLER SONAR APPARATUS

BACKGROUND OF THE INVENTION

1. Field of the Invention

The present invention relates to Doppler sonar apparatus, and more specifically to marine Doppler sonar apparatus for use in deep water.

2. Description of the Prior Art

Marine Doppler sonar apparatus for navigation, speed measurement, and the like is well known in the art. In general, such apparatus includes means for projecting an acoustic beam angularly downward toward the ocean bottom. Energy reflected from the bottom returns to the sonar apparatus in which it is analyzed and processed to obtain the desired information.

In relatively shallow water, the reflected signal is sufficiently strong to permit accurate analysis. However in deep water, the signal is highly attenuated so that the signal reaching the sonar apparatus is inadequate to provide accurate measurements.

One means for providing usable measurements in deep as well as shallow water is disclosed in U.S. Pat. No. 3,795,893 issued to J. A. Kritz and S. D. Lerner. In this apparatus, signals are reflected from the bottom in relatively shallow water. In deeper water, gating means are used to sample reflections arising from discontinuities present in the sea water at specified distances from the vessel. U.S. Pat. No. 3,795,893 also illustrates a "Janus" type installation wherein pairs of acoustic beams are launched angularly toward the ocean bottom so as to have components in opposite horizontal directions. Horizontal motion of the ship in the plane of the beams is detected by an increase in frequency in the reflected signal arising from one beam, and a decrease in frequency in the other reflected signal.

Alternatively, parametric arrays have been proposed for use in deep water. The basic theory for parametric operation was described, for instance, by P. J. Westerveldt in an article appearing in Vol. 35 of the Journal of the Acoustical Society of America in April, 1963 and entitled: "Parametric Acoustic Array." In this article, Westerveldt proposed launching difference frequency waves by two highly collimated sound beams. According to Westerveldt's theory, the absorptive properties of the propagation medium would attenuate the high frequency waves and permit the resultant low frequency wave to propagate in an area remote from the source.

In a second article in Vol. 55 of the same Journal, dated January 1974, and entitled "On the Performance of a Dual Frequency Parametric Source," F. H. Fenlon presented a theoretical discussion relating to the formation of a farfield difference frequency signal resulting from the non-linear interaction in the propagation medium when two different frequency primary waves are radiated simultaneously by a finite amplitude source. Various arrangements for providing practical parametric arrays for marine use have been tried. In some of these designs, an acoustic converging lens is used to collect reflected acoustic energy and focus this energy on transducers placed in the focal plane of the lens. However, in such an arrangement, the transducers should be made relatively small in order to be fully irradiated by the concentrated sound waves. If such transducers are then used to generate the required high power acoustic wave, such transducers are subject to extreme cavitation and resultant failure because of their small radiating area. Furthermore, the simultaneous production of multiple high power beams can cause cavitation in the region of beam intersection.

The present invention provides means to overcome these shortcomings.

SUMMARY OF THE INVENTION

A solid acoustic lens having a flat disk-like central portion and a double concave outer portion is used in combination with a plurality of sonic transducers having high power-large radiating surfaces to produce large amplitude collimated beams that pass through the central portion of the lens. The entire lens aperture is used to capture energy reflected from a remote target. Phasing means prevent the summation of pressure maxima at the lens center so as to avoid cavitation.

DESCRIPTION OF THE PREFERRED EMBODIMENTS

Figure 1:
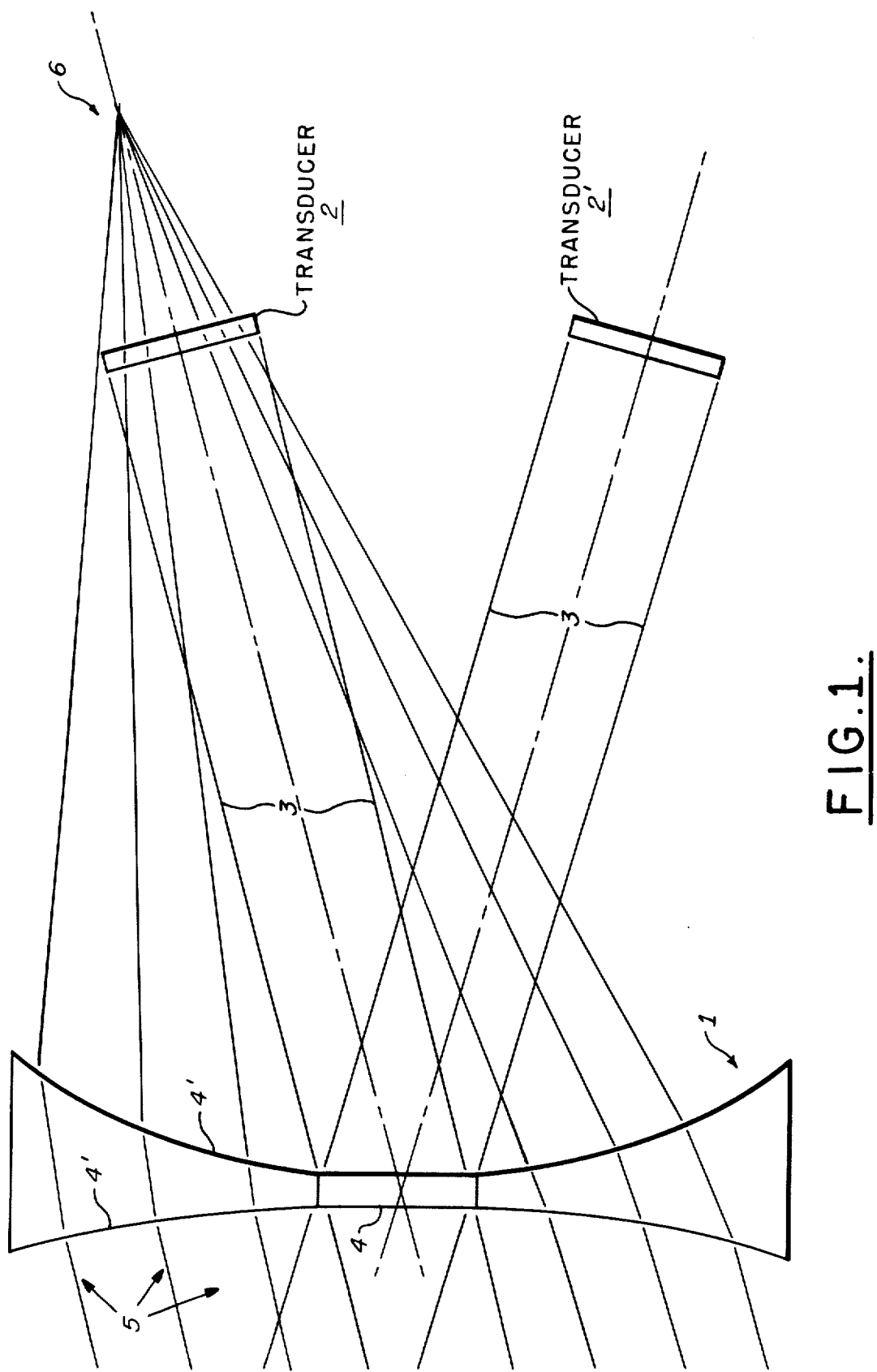
FIG. 1 is a diagram illustrating the principles of the invention.

In the application of Doppler sonar technology, it is necessary to form narrow beams of acoustic energy in certain desired directions. Narrow beams are projected by electroacoustic transducers when the size of the radiating transducer aperture is large compared to a wave length.

Doppler sonars operating at moderate heights above the ocean bottom may employ higher frequency sound waves than those which are designed to reach the full ocean depths due to the increased absorption losses of the ocean medium with the increase in frequency. Since the wave length is reciprocally related to the frequency, large radiating surfaces are required to produce narrow beams for Doppler sonars designed to operate off the ocean bottom in deep water. For example, a 3° beam can be formed at 200 KHz with a 15.2 cm radiator for operation in water depths up to 300 meters. For depths in the order of 6 Km, a frequency of 10 KHz is necessary, and a 3° beam requires a radiating aperture of some 3 meters in diameter.

Since such large transducers are obviously impractical, non-linear acoustics in the form of a parametric array have been proposed as a means for generating a low frequency beam with small radiating apertures. This technique utilizes the non-linear property of water in generating a narrow beam of low frequency acoustic energy by the interaction of two high frequency collinear beams of slightly different frequency. For example, the 3°-200 KHz, 15.2 cm. transducer mentioned previously can be energized with two frequencies such as 205 KHz and 195 KHz, and by virtue of the nonlinearity of the ocean water, produce a secondary beam of 10 KHz sound in the far field having a divergence only in the order of 4°. However, in such systems the conversion efficiency is low so that considerable power must be generated in the primary beams to produce a secondary beam with sufficient energy to perform effectively.

But, the great advantage offered by the parametric array in reducing the size of the acoustic projectors is limited by the fact that the electroacoustic transducer must respond to very weak return signals from the ocean bottom. In all sonar signalling devices, it is desirable to have a large receiving aperture in order to capture as much of the returned signal energy as possible. This so called "directivity index" implies again that a large transducer aperture, and therefore, high directivity, narrow beams are desirable to increase the signal and reduce the background noise. For example, an aperture having a diameter of some 76 cm. is desired in order to provide sufficient signal-to-noise ratio at 10 KHz to implement a parametric array, four beam system for deep sea operation. Thus even though the prior art suggests the use of relatively small parametric transducers for launching the acoustic waves, relatively large receiving devices would be necessary. For example, in a system employing the four 15.2 cm. parametric transducers previously mentioned, four 76 cm. receiving devices of a single 76 cm. phased array would be necessary. But such large phased arrays and multiple receiving devices represent unwanted complexity, size and cost. The present invention provides a means for achieving large aperture and high directivity in a multiple beam system with reduced size, complexity and cost.

The prior art suggests the use of a converging lens in combination with a number of small transducers equal to the number of beams to be generated, each transducer being positioned in the focal plane of the lens. However, since the transducers in such an arrangement are placed at a focal point, they must necessarily be small in diameter in order to irradiate the lens with a spherical wave front so that a narrow beam plane wave is produced. Since parametric generation requires high power in order to obtain reasonable secondary beam energies, such a prior art arrangement would cause severe cavitation problems at the small transducer working face.

In the present invention, advantage is taken of the ability of a lens to gather energy incident across a wide aperture and to focus this energy on a small region. Incident plane parallel rays from a specific direction maintain their orientation relative to the lens so that multiple transducers positioned within the focal length of the lens are able to receive energy from specific directions defined by the angle made between the lens axis and the line between the center of the lens and the transducer. Since the transducers are not placed in the focal plane, they can be made sufficiently large to accommodate the relatively high power requirements and at the same time produce a collimated beam that propagates through a central planar section of the lens.

FIG. 1 depicts a presently preferred lens-transducer arrangement useful in practicing the invention. An acoustic lens 1 is used with a number of parametric transducers 2 whose surface areas are consistent with the power handling requirements of a proposed application. In transmission, these transducers are large enough to produce sharp collimated beams 3 at the high primary beam frequency and power. The collimated beams pass unaltered through a flat section 4 in the center of a lens 1.

As depicted in FIG. 1, the acoustic lens may be considered a hybrid lens in that it includes a central disklike portion 4 surrounded by an annular converging portion defined by double concave surfaces 4'.

The annular converging portion of the lens serves to concentrate the signal reflected from the ocean bottom on the transducers. The central disk-like portion serves as a "neutral" portion in that it permits the collimated beams 3 to pass through this area with essentially no alteration.

Thus incoming parallel rays 5 pass through the annular curved portions of the lens and converge towards the focal point 6. However, since the transducer 2 is placed within the focal length of the lens, these rays are distributed across the transducer surface. The small region of parallel rays entering the center flat "neutral" portion of the lens proceed to the transducer with only minor phase deviation from the peripheral rays and do not materially affect the receiving capability. Because of the relatively large transducer area, the transducer intercepts essentially all of the incoming rays intended for that transducer even though the transducer is positioned ahead of the focal point of the lens. Since the transducer is thus positioned closer to the lens than the focal point, this also reduces the depth of the assembly. Such a reduction in depth becomes important in ship installations where the lens is flush with the hull of the vessel and the depth of the assembly determines the space needed to accommodate the installation.

It should be noted that the advancement of the transducer toward the lens could be ideally accommodated only if the surface of the transducer were spherical and had a radius of curvature equal to the distance of that surface from the true focal point since only under such circumstances would the transducer surface receive all rays in phase and thus in an additive relationship. However, it should be noted that in accordance with the principles of the invention, the plane surface may be used because the phase deviation is rendered very small by virtue of the comparatively low frequency of the received signals. The plane surface transducer is preferred because such a transducer is easily fabricated and results in a more economical structure. It should be noted that the flat central portion of the lens could be eliminated so that the beams 3 actually pass through a hole in the lens. However, such an arrangement is not ordinarily preferred because it could produce hydrodynamic disturbances along the bottom of the ship with a consequent impairment of equipment and ship performance.

The lens itself is most conveniently fabricated from plastic materials such as polystyrene, methyl methacrylate, or syntactic epoxy foam, whose specific acoustic impedances do not differ materially from water, and whose acoustic absorption is low. Because the propagation velocities of such materials are higher than water, these materials show refractive indices less than 1.0. For this reason, the curvatures in the annular portion of the lens are the negative of those that would ordinarily be expected in optical lens designs.

In accordance with known parametric techniques, each transducer is energized by dual frequency signals to produce a transmitted beam. Because of the non-linear property of the water, a secondary beam is formed in an area remote from the hull of the vessel. This secondary beam has a frequency equal to the difference in the primary frequencies used to energize the transducers. The secondary beam is reflected from the ocean bottom and returns to the area of the lens where it is directed onto the particular transducer from which the signal originated.

Typically, the configuration depicted in FIG. 1 would have the following parameters:

Primary Frequencies—two frequencies centered about 200 KHz.
Secondary Frequencies—0-20 KHz.
Primary Power—200 watts per frequency.
Transducers—Circular piston, 15.2 cm. diameter.
Configuration—4 beams 15° off axis in two perpendicular planes.
Lens Description:
Material—Polystyrene
Focal Length=1.4 meters—double concave, minimum spherical aberration design.
Radii of curvature: 172 cm.; 68 cm.
Transducer to Lens Spacing: 99 cm.

It will be recalled that each of the transducers is energized from a dual frequency source which will be described.

Figure 2:
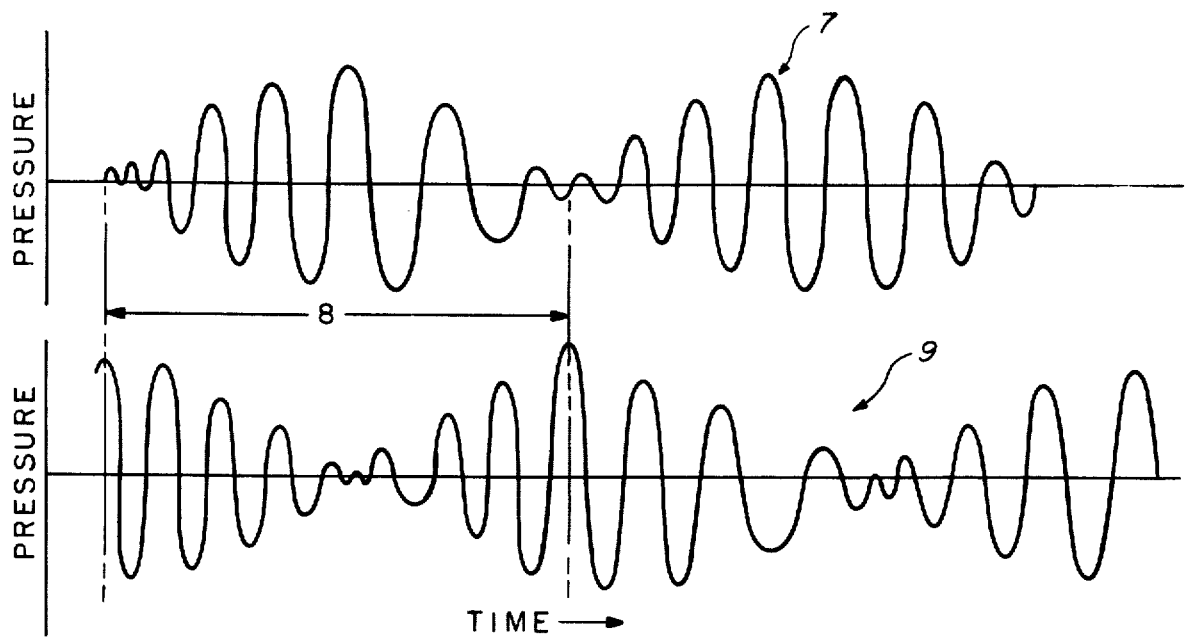
FIG. 2 is an illustration of pressure variations produced by a transmitting transducer in a parametric system.

Referring now to FIG. 2, wave 7 represents the pressure wave emitted from one transmitting transducer in the system. In accordance with well known principles, wave 7 is essentially a sinusoidally modulated sine wave, since it represents the sum of two primary sine waves of slightly different frequency.

Periodic reinforcement occurs when the phases add, and cancel when they subtract. The time period 8 represents the period of the difference (secondary) frequency, which signal is created by the demodulating effect occurring in the water column due to the non-linearity of that medium. Similarly, wave 9 of FIG. 2 represents the pressure wave drawn to the same time scale as wave 7, where one of the primary sine waves is shifted in phase by 180°. As will be explained, this 180° phase shift is desirable since, as can be seen from FIG. 2, the pressure maxima of one wave then occur simultaneously with the pressure minima of the other wave.

It should also be noted from FIG. 2, that despite the fact that the phase shift is performed at the primary high frequency, the desired phase alteration occurs at the low, secondary frequency time scale. This permits the non-coincidence of pressure maxima to be maintained for a half secondary wave length of path difference in physical space, so that a whole region around the lens center 4 can be free of the sum of two pressure maxima. For example, in a system such as described previously, with a difference of frequency of 10 KHz, two transducers, positioned 99 cm from the lens center and spaced 56 cm apart would not experience phase coincidence until the waves reach a distance of 13.5 cm from the lens center. This distance is almost twice the width of the intersection of the two collimated beams in that region.

In a Janus system employing four transducers equally spaced around the lens axis, the second pair of transducers would preferably be energized so that the primary phase of the first transducer of this pair is shifted 90° and the primary phase of the second of these transducers is shifted 270° so as to maintain the 180° difference within the second pair. In this way, no two of the four emissions will have their peak pressure amplitudes add in the lens center.

Figure 3:
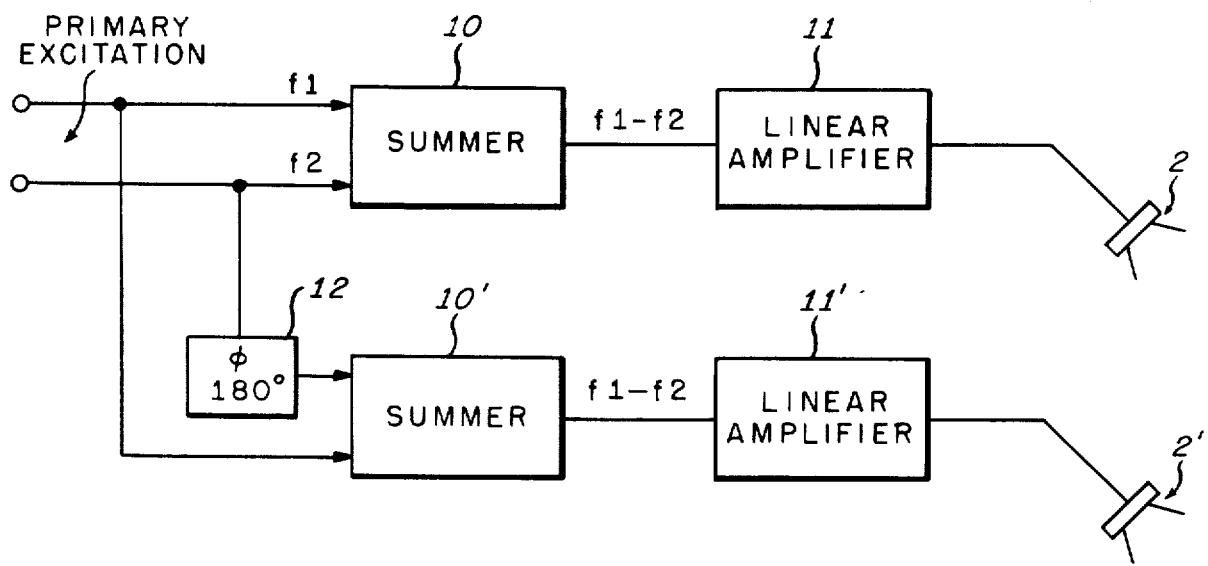
Figure 4:
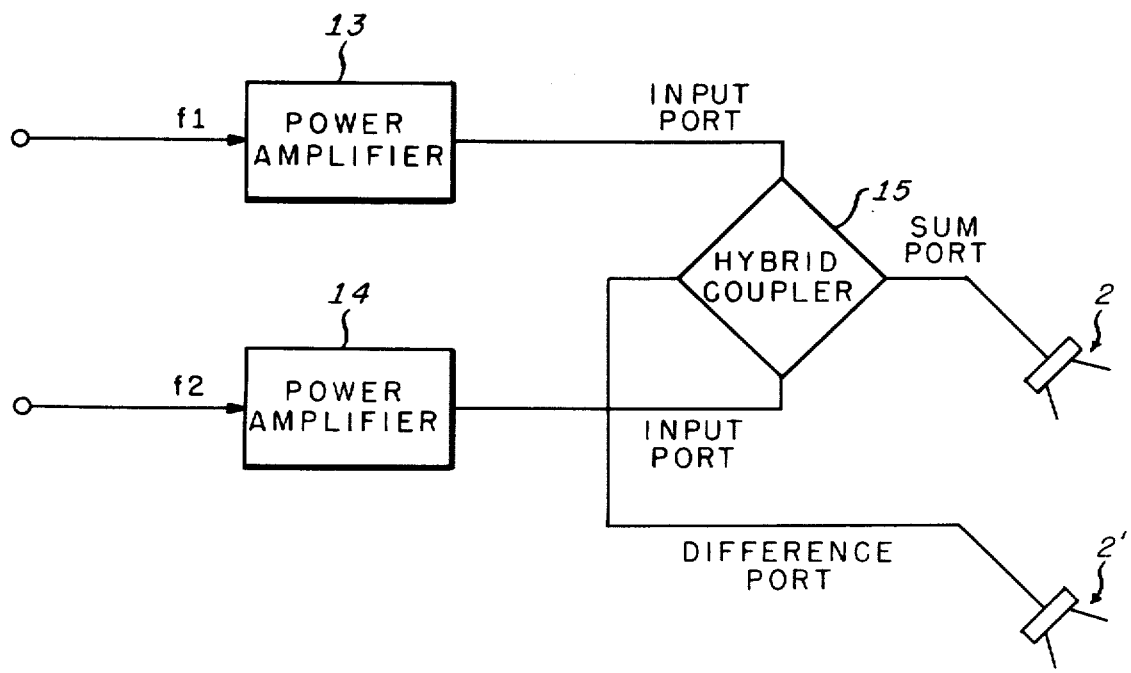

FIGS. 3 and 4 are schematic representations of circuits for coupling the transducers to a power source for achieving the phase relationships depicted in FIG. 2. In the circuit of FIG. 3, two signals $f_1$ and $f_2$, each of which represents a desired primary frequency, are summed in a summing network. Such summing networks are well known in the art and provide an analogue signal representing a simple sum of two sinusoidal signals and corresponding, for instance, to the pressure wave form 7 depicted in FIG. 2. The output of the summing network 10 is applied through a linear amplifier 11 to a transducer 2.

The primary excitation frequency $f_1$ is also applied to a second summing network 10'. The primary excitation signal $f_2$ is also applied through a 180° phase shifter 12 to the summing network 10' to provide a phase-shifted sum frequency. This latter signal is applied through a linear amplifier 11' to the transducer 2' so that the transducer pair 2 and 2' thus provide output signals having the phase relationship illustrated by wave-forms 7 and 9 of FIG. 2.

It will be appreciated by those skilled in the art, that although the previous discussion has been concerned with a pair of transducers 2 and 2' a combination of three or more transducers may be desired. In such instances, each additional transducer would be energized through individual summing networks, linear amplifiers, and phase shifters. However, the phase shifters in such applications would be adjusted to provide correspondingly smaller phase shifts so that the beams radiated from the individual transducers in the given combination have equiangular phase displacements with respect to each other.

Alternatively, the presently preferred circuit of FIG. 4 may be used to couple the primary excitation frequencies to the pair of transducers 2 and 2'. In the circuit of FIG. 4, the primary excitation frequencies $f_1$ and $f_2$ are applied through individual power amplifiers 13 and 14 through a conventional hybrid coupler 15. The output signals from the sum and difference ports of the hybrid coupler are applied to the transducers 2 and 2' respectively. The circuit of FIG. 4 has an advantage in that linear amplifiers are not necessary since only constant level, primary excitation signals are amplified prior to summing. The amplifiers are required to provide the desired output level but need not reproduce a varying envelope with fidelity. Summation is accomplished at high level by means of the hybrid coupler 15, which is a four port device in which two ports are inputs and two output ports deliver a signal equivalent to the combination of the primary excitation signals respectively. Hybrid couplers of various types are well known to those skilled in the art, but in general, such couplers are versions of a balanced electrical bridge and are generally commercially available in various power and frequency ratings.

Figure 5:
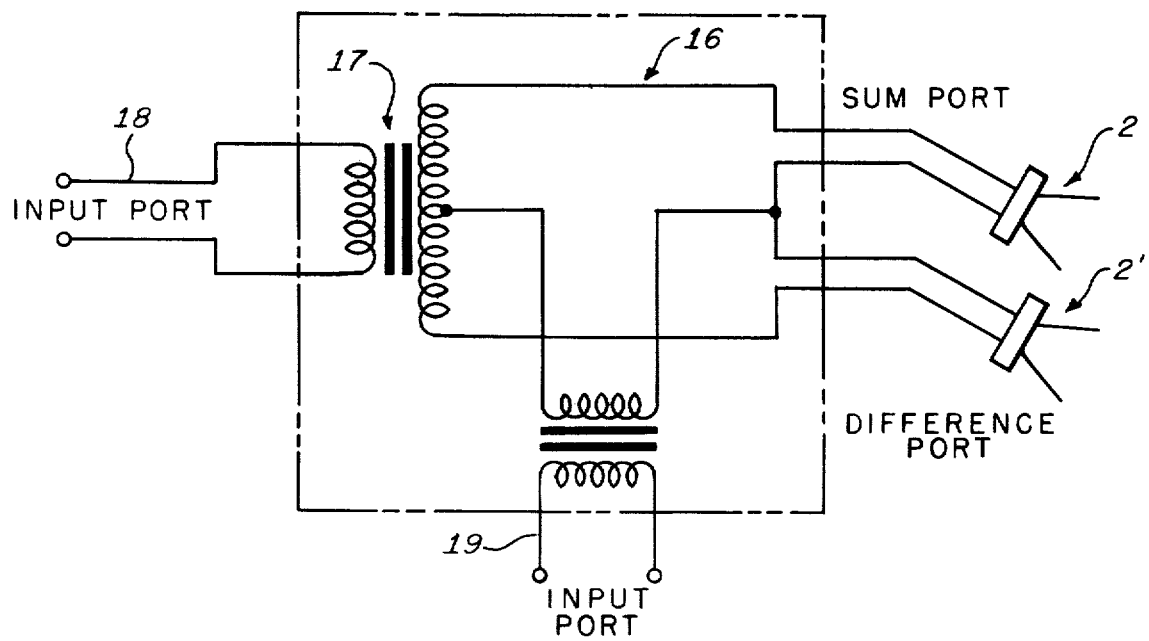
FIGS. 3-5 are diagrams illustrating means for energizing the transducers.

One suitable type of hybrid coupler is illustrated in FIG. 5 by way of example. This coupler consists essentially of a balanced bridge 16 energized through an accurately center-tapped transformer 17. The input signals are applied to the input ports 18 and 19 respectively, and output signals are taken from the sum and difference ports. The transformer 17 is designed for correct scaling of the input voltage usually provided with suitable ground isolation.

Figure 6:
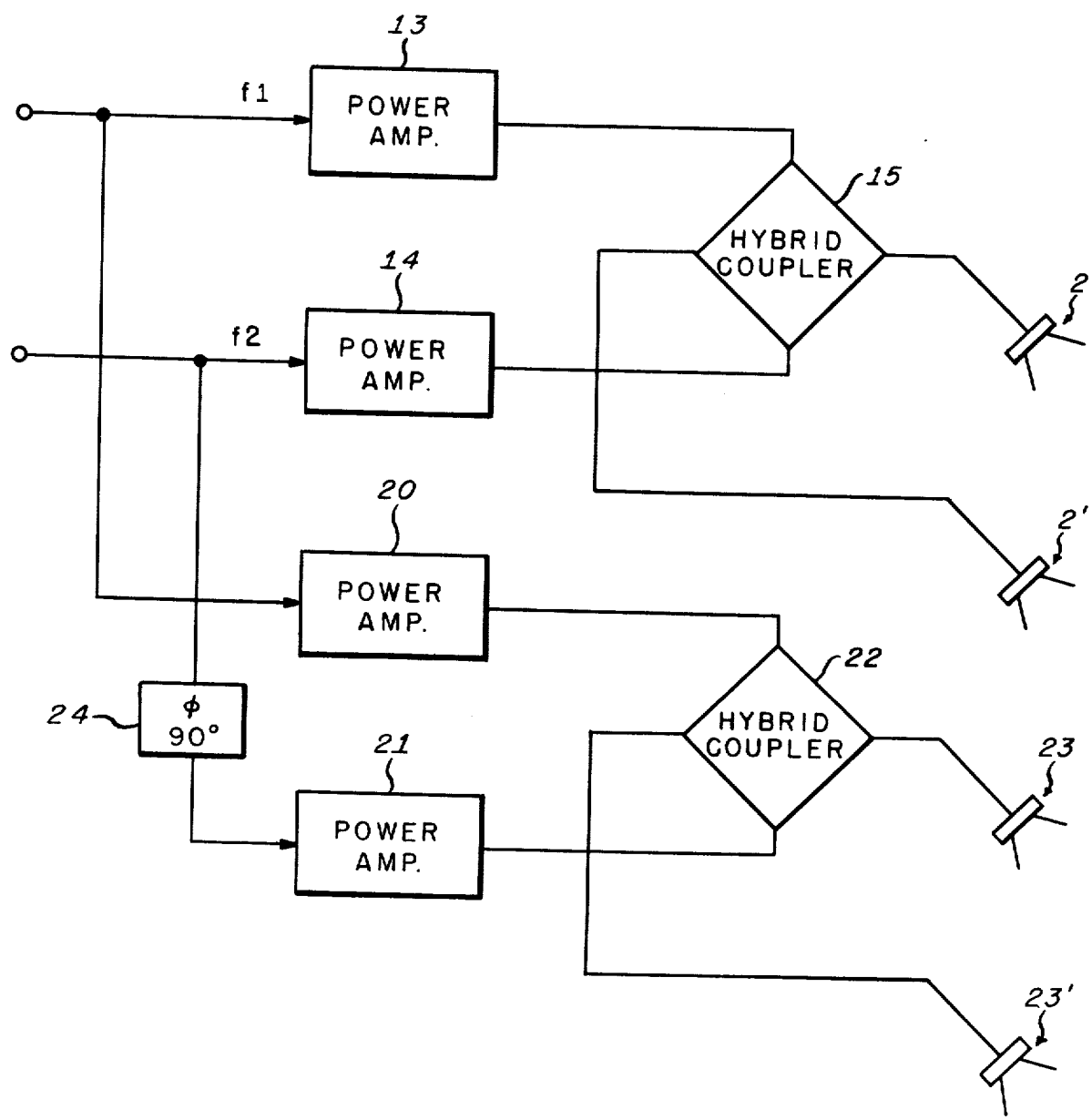
FIG. 6 is a diagram illustrating a circuit useful in a Janus system.

FIG. 6 illustrates a circuit for energizing a four beam system such as a "Janus" doppler sonar system and utilizing the type of driving circuit illustrated in FIG. 4. In addition to the power amplifiers 13 and 14 and the hybrid coupler 15 for driving the transducers 2 and 2' previously described with respect to FIG. 4, the circuit of FIG. 6 includes additional power amplifiers 20 and 21 connected to drive a hybrid coupler 22 so as to energize the second pair of transducers 23 and 23'. The power amplifiers, hybrid coupler, and transducers are similar to the corresponding elements of FIG. 4, however the power amplifier 21 is driven from the primary excitation frequency $f_2$ through a 90° phase shifter 24. By means of the circuit of FIG. 6, each pair of transducers 2, 2' and 23, 23' produce a pair of output waves as illustrated by wave forms 7 and 9 in FIG. 2. However the pair of waves produced by the transducers 23 and 23' are shifted 90° in time with respect to the pair of waves produced by the transducers 2 and 2'. This 90° phase displacement shifts the maxima of one set of waves away from the maxima of the other set of waves by an amount equal to ¼ of the wave length 8 illustrated in FIG. 2 and thus avoids reinforcement between individual waves.

The present invention provides a practical means for operating a parametric doppler sonar system in deep water. The high power required in such a system is made possible by utilizing relatively large aperture transducers in combination with the specialized lens containing a neutral central portion that permits substantially undisturbed propagation of the primary beam, and a converging portion that serves to collect the low power return signal and to concentrate this signal on a transducer. By positioning the transducers ahead of the focal plane of the lens, the relatively large transducer is able to intercept substantially all of the return energy in a given beam. Cavitation problems in the water medium that might arise because of the high power requirements in multibeam systems are avoided by phasing the individual acoustic waves so as to prevent reinforcement of the individual waves in the area of the beam intersections.

While the invention has been described in its preferred embodiments, it is to be understood that the words which have been used are words of description rather than limitation and that changes within the purview of the appended claims may be made without departing from the true scope and spirit of the invention in its broader aspects.

I claim:

1. Parametric array Doppler sonar apparatus comprising a plurality of piston-type transducers, each being positioned to launch and receive acoustic energy along a different specified axis, means to energize each transducer during specified time intervals with a signal comprising a combination of first and second primary excitation frequencies,
    a hybrid acoustic lens having a central disk shaped portion and an annular ray-converging portion surrounding said central portion,
    each of said transducers having a diameter sufficiently large to launch a substantially collimated acoustic beam along the axis of that transducer and being oriented to direct the collimated beam through the central portion of said lens,
    each of said transducers being further positioned within the focal region of the converging portion of said lens so as to intercept substantially all of the acoustic energy reflected from a remote target and passing through the lens along the axis of that transducer.

2. The sonar apparatus of claim 1 wherein the plurality of transducers includes a pair of transducers, and the means to energize these transducers includes means to provide a signal equal to the instantaneous sum of said first and second signals to the transducers.

3. The sonar apparatus of claim 2 wherein the means to energize the pair of transducers further includes means to shift the phase of the signal applied to one of the transducers in said pair 180° with respect to the signal applied to the other of the transducers in said pair.

4. The sonar apparatus of claim 1 wherein the plurality of transducers includes two pairs of transducers arranged for operation in a Janus system.

5. The sonar apparatus of claim 4 further characterized in that the means to energize the transducers includes means to shift the phase of the signal applied to one of the transducers in each pair 180° with respect to the signal applied to the other transducer in that pair and further includes means to shift the phase of the signals applied to one pair of transducers 90° with respect to the signals applied to the other pair of said transducers.

6. The sonar apparatus of claim 1 wherein the plurality of transducers includes a pair of transducers, and the means to energize the transducers includes individual summing means responsive to said first and second signals and individual linear amplifier means responsive to the output of the corresponding summing means for energizing each transducer, said energizing means further including phase shifting means for reversing the phase of said second signal before this signal is applied to one of said summing means.

7. The sonar apparatus of claim 1 wherein the plurality of transducers includes a pair of transducers and the means to energize the transducers includes individual power amplifiers coupled to receive said first and second signals respectively, and a hybrid coupler having first and second input ports, and sum and difference output ports, said first and second input ports being coupled to receive the output signals from the first and second of said power amplifiers, respectively, said sum and difference output ports being coupled to energize the first and second of the transducers in said pair respectively.

8. The sonar apparatus of claim 1 wherein the lens is fabricated from a material having an acoustic velocity of propagation greater than that of water and wherein said annular portion is constructed in the form of a double concave lens.

9. The sonar apparatus of claim 8 wherein the lens is constructed from methyl methacrylate.

10. The sonar apparatus of claim 8 wherein the lens is constructed from syntactic epoxy foam.

11. The sonar apparatus of claim 8 wherein the lens is constructed from polystyrene.

12. The sonar apparatus of claim 11 wherein the annular portion of the lens is constructed to provide a focal length of 1.4 meters and the transducers are positioned 99 cm from the lens.

* * * * *